United States Patent
Charra et al.

(10) Patent No.: US 9,957,207 B2
(45) Date of Patent: May 1, 2018

(54) PROCESS FOR THE SELECTIVE HYDROGENATION OF OLEFINIC FEEDS WITH A SINGLE PRINCIPAL REACTOR AND A GUARD REACTOR OF REDUCED SIZE

(71) Applicant: IFP Energies Nouvelles, Rueil-Malmaison (FR)

(72) Inventors: Cyprien Charra, Lyons (FR); Adrien Mekki-Berrada, St Etienne (FR); Frederic Bazer-Bachi, Irigny (FR); Beatrice Fischer, Lyons (FR); Florian Hilly, Neuilly sur Seine (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days. days.

(21) Appl. No.: 15/388,220

(22) Filed: Dec. 22, 2016

(65) Prior Publication Data
US 2017/0174585 A1    Jun. 22, 2017

(30) Foreign Application Priority Data
Dec. 22, 2015   (FR) ...................................... 15 63022

(51) Int. Cl.
*C07C 5/03* (2006.01)
*B01J 8/04* (2006.01)
(Continued)

(52) U.S. Cl.
CPC .................. *C07C 5/03* (2013.01); *B01J 8/04* (2013.01); *C10G 45/32* (2013.01); *C10G 65/02* (2013.01)

(58) Field of Classification Search
CPC ..... B01J 8/04; B01J 23/44; B01J 23/66; B01J 23/96; B01J 38/10; B01J 8/0457;
(Continued)

(56) References Cited

U.S. PATENT DOCUMENTS

| 4,118,310 A | 10/1978 | Frayer et al. |
| 6,306,287 B1 | 10/2001 | Billon et al. |

(Continued)

FOREIGN PATENT DOCUMENTS

| FR | 2784687 A1 | 4/2000 |
| FR | 2810991 A1 | 1/2002 |

(Continued)

OTHER PUBLICATIONS

Search Report dated Sep. 6, 2016 issued in corresponding FR 1563022 application (2 pages).

*Primary Examiner* — Sharon Pregler
(74) *Attorney, Agent, or Firm* — Millen, White, Zelano and Branigan, P.C.

(57) ABSTRACT

The present invention relates to a process for the selective hydrogenation of a feed of hydrocarbons containing polyunsaturated molecules comprising at least 3 carbon atoms, using a single principal fixed bed reactor R1 containing at least two catalytic beds A1 and A2 and a fixed bed guard reactor which is reduced in size, said hydrogenation reactors being disposed in series for use in a cyclic manner in accordance with a sequence of steps which can be used to short-circuit the catalytic bed or beds of the principal reactor which have been at least partially deactivated with the aid of the guard reactor, while ensuring the continuous operation of the process.

15 Claims, 2 Drawing Sheets

(51) Int. Cl.
*C10G 45/32* (2006.01)
*C10G 65/02* (2006.01)

(58) Field of Classification Search
CPC ........... C07C 5/03; C07C 7/163; C07C 7/167; C07C 11/06; C07C 11/167; C10G 45/32; C10G 65/02
See application file for complete search history.

(56) References Cited

U.S. PATENT DOCUMENTS

| | | |
|---|---|---|
| 6,693,225 B2 | 2/2004 | Boyer et al. |
| 2002/0022754 A1 | 2/2002 | Boyer et al. |
| 2013/0165711 A1* | 6/2013 | Dandeu .................... C07C 5/03 585/251 |
| 2014/0001089 A1 | 1/2014 | Bazer-Bachi et al. |

FOREIGN PATENT DOCUMENTS

| | | |
|---|---|---|
| FR | 2970260 A1 | 7/2012 |
| FR | 2984915 A1 | 6/2013 |

\* cited by examiner

PROCESS FOR THE SELECTIVE HYDROGENATION OF OLEFINIC FEEDS WITH A SINGLE PRINCIPAL REACTOR AND A GUARD REACTOR OF REDUCED SIZE

The present invention relates to a process for the selective hydrogenation of a feed of hydrocarbons containing polyunsaturated molecules comprising at least 3 carbon atoms, using a single principal fixed bed hydrogenation reactor containing at least two catalytic beds and a fixed bed guard hydrogenation reactor which is reduced in size, said hydrogenation reactors being disposed in series for use in a cyclic manner in accordance with a sequence of steps which can be used to short-circuit the catalytic bed or beds of the principal reactor which have been at least partially deactivated with the aid of the guard reactor while ensuring the continuous operation of the process.

Organic mono-unsaturated compounds such as ethylene and propylene, for example, are the source of the manufacture of polymers, plastic materials and other added value chemical products. These compounds are obtained from natural gas, naphtha or gas oil which have been treated by steam cracking or catalytic cracking processes. These processes are operated at high temperature and produce a large variety of desired mono-unsaturated molecules such as ethylene, propylene, linear butenes, isobutene, pentenes as well as unsaturated molecules containing up to approximately 15 carbon atoms.

At the same time, polyunsaturated compounds such as acetylene, propadiene and methylacetylene (or propyne), 1-2 butadiene and 1-3 butadiene, vinylacetylene and ethylacetylene, and other polyunsaturated compounds with a boiling point corresponding to the gasoline fraction C5+ (gasolines containing hydrocarbon compounds containing 5 or more carbon atoms), in particular styrene or indene compounds, are also formed. These polyunsaturated compounds are highly reactive and lead to unwanted reactions in the polymerization units. Thus, it is necessary to eliminate them before upgrading these cuts. In the case of a pyrolysis gasoline feed, these compounds have to be eliminated before the hydrodesulphurization treatment which is conventionally subsequently carried out.

Selective hydrogenation is the principal treatment which has been developed to specifically eliminate unwanted polyunsaturated compounds from these hydrocarbon feeds.

The selective hydrogenation of unsaturated hydrocarbons can be used to selectively hydrogenate the polyunsaturated compounds present in the feed to be treated in a manner such that the diolefinic or acetylenic compounds are partially hydrogenated into monoolefins and that the styrene and indene compounds present in the gasoline cuts are partially hydrogenated into the corresponding aromatic compounds, avoiding their complete saturation in order to avoid the formation of the corresponding alkanes or naphthenes.

Conventional units for the selective hydrogenation of unsaturated hydrocarbons generally comprise a principal hydrogenation section comprising a fixed bed catalytic reactor in which the liquid hydrocarbon feeds are brought into contact with gaseous hydrogen (two-phase reactor, or monophase reactor when all of the hydrogen can be dissolved in the feed).

At the same time as these selective hydrogenation reactions, secondary reactions may lead to the formation of oligomers which can lead to the deposition of gums on the surface of the catalyst, causing its gradual deactivation. In addition, the impurities contained in the feed may cause a deactivation of the catalyst. This means that the catalyst has to be regenerated in order to regain its efficiency. For this reason, conventional selective hydrogenation units generally comprise a second fixed bed reactor towards which the hydrogenation reaction is redirected when the first reactor has to be reactivated or regenerated.

The document FR 2 984 915 describes a process for the selective hydrogenation of an unsaturated olefinic feed containing 3 or 4 carbon atoms using at least two principal fixed bed reactors which can be permutated, each containing at least one catalytic bed and in which said olefinic feed passes in succession through all of the reactors and in which, each time that one of the reactors is deactivated, the point of introduction of the feed is displaced downstream. That document thus proposes optimizing facilities for the selective hydrogenation of unsaturated hydrocarbons by using reactors which can be disposed in series in the principal hydrogenation section without in any way having to interrupt the catalyst regeneration process.

However, the process described in FR 2 984 915 necessitates at least two principal reactors of identical size in which only one of the reactors is carrying out hydrogenation, while the second (also termed the "spare") is regenerated. This second reactor, although it is present in the facility, is thus not used for hydrogenation of the feed when the catalyst of the first reactor has not been deactivated.

The present invention proposes optimizing the processes for the selective hydrogenation of unsaturated hydrocarbons by proposing the use of a single principal reactor and a smaller sized guard reactor, said reactors being disposed in series for use in a cyclic manner in accordance with a sequence of steps which mean that the catalytic beds of the principal reactor which have been at least partially deactivated can be short-circuited with the aid of the guard reactor while ensuring continuous operation of the process.

Thus, the present application pertains to a process for the selective hydrogenation of a feed of hydrocarbons containing polyunsaturated molecules comprising at least 3 carbon atoms, in which said feed and a gaseous phase comprising hydrogen are passed, under hydrogenation conditions, over a hydrogenation catalyst in a single principal fixed bed reactor containing at least two catalytic beds and a fixed bed guard reactor which is smaller in size containing at least one catalytic bed, said reactors being disposed in series for use in a cyclic manner by repeating the steps a), b), c), c'), d) and d') defined below in succession:

- a step a), during which the feed passes in succession through all of the catalytic beds of the principal reactor, when the first catalytic bed of the principal reactor starts to become deactivated, a step b), during which the feed is introduced into the guard reactor then, by short-circuiting the first partially deactivated catalytic bed of the principal reactor, into the next non-deactivated catalytic bed of said principal reactor located immediately downstream with respect to the direction of movement of the feed,
- a step c), during which the feed passes uniquely and successively through all of the catalytic beds of the principal reactor,
- a step c'), simultaneously with step c), during which the deactivated catalyst of the catalytic bed or beds of the guard reactor is regenerated and/or replaced with fresh catalyst,
- a step d), during which the feed only passes through the guard reactor, a step d'), simultaneously with step d), during which the deactivated catalyst of the at least two catalytic beds of the principal reactor is regenerated and/or replaced with fresh catalyst.

The selective hydrogenation process in accordance with the invention thus does not need a second principal reactor, which represents a saving on investment costs and on operating costs. In fact, while the process of the invention requires a guard reactor, it is of reduced size compared with a second principal reactor.

Compared with a selective hydrogenation process functioning with a single principal reactor (without a reduced size guard reactor), the process in accordance with the invention can be used to increase the treatment capacity of the feed as well as to increase the cycle time for the same catalytic volume. In addition, it is not necessary to stop the process during regeneration of the catalyst of one of the reactors. Thus, this process is particularly useful when it is desired to increase the capacity of existing units ("revamping") in an inexpensive manner. The process in accordance with the invention can be used to increase the cycle time by slowing down the formation of oligomers (or gums) which increases the deactivation of the catalyst.

In addition, the selective hydrogenation process in accordance with the invention can be used to provide flexibility during operation, both in terms of cuts which are more difficult to treat and in terms of changes in capacity.

In accordance with a variation, the total volume of catalyst contained in the catalytic bed or beds of the guard reactor is a maximum of 60% of the total volume of catalyst contained in the catalytic beds of the principal reactor.

In accordance with a variation, the hydrocarbon feed is selected from the group constituted by a C3 cut from steam cracking, a C4 cut from steam cracking, a C5 cut from steam cracking and a pyrolysis gasoline, and a mixture thereof.

In accordance with a variation, the period of operation for each of steps a), b), c) and d), defined with respect to a maximum operating period $t_{max}$ for each step, which is the time to reach a maximum tolerable value for a temperature or a selectivity for a given feed, is respectively:

for step a): between 10% and 70% of $t_{Amax}$
for step b): between 40% and 100% of $t_{Bmax}$
for step c): between 90% and 100% of $t_{Cmax}$
for step d): between 70% and 100% of $t_{Dmax}$.

In accordance with a variation, the maximum tolerable value for a C3 feed is the selectivity in accordance with the specifications in force, the maximum tolerable value for a C4 feed is a maximum temperature of 160° C., the maximum tolerable value for a C5 feed is a maximum temperature of 160° C., and the maximum tolerable value for a feed of pyrolysis gasoline is a maximum temperature of 200° C.

In accordance with a variation, each reactor is operated at a temperature of 0° C. to 200° C., at a pressure in the range 1 to 6.5 MPa and at an overall hourly space velocity, defined as the ratio of the volume flow rate of the fresh feed at 15° C. to the total volume of catalyst present in the series of reactors employed, in the range 1 $h^{-1}$ to 100 $h^{-1}$.

In accordance with a variation, a portion of the effluent obtained from the principal reactor or from the guard reactor is recycled as a mixture with the feed to be hydrogenated.

In accordance with a variation, the operating conditions for hydrogenation during steps a) b) c) and d) are identical.

In accordance with another variation, during step d), the temperature of the guard reactor is increased and/or the flow of the phase comprising hydrogen is increased, and/or the recycle flow rate into the guard reactor is increased and/or the flow rate of feed introduced into the guard reactor is reduced with respect to respectively the temperature, the flow or the flow rate(s) employed at the start of step a).

In accordance with a variation, the increase in the temperature of the guard reactor at the head of the reactor at the start of step d) with respect to the start of step a) is in the range 0.5° C. to 40° C.

In accordance with a variation, the increase in the recycle flow rate at the guard reactor at the start of step d) with respect to the recycle flow rate at the start of step a) is in the range 0.5% to 100%.

In accordance with a variation, a quench is introduced between two catalytic beds in the principal reactor or the guard reactor, said quench possibly being a liquid quench and/or a gaseous quench.

In accordance with a variation, one or more heat exchanger(s) is employed between the guard reactor and the principal reactor.

In accordance with a variation, the hydrogenation catalysts used are identical or different in the catalytic bed or beds of the principal reactor and/or of the guard reactor.

DETAILED DESCRIPTION

The present invention concerns a process for the selective hydrogenation of a feed of hydrocarbons containing polyunsaturated molecules comprising at least 3 carbon atoms, using a single principal fixed bed reactor containing at least two catalytic beds and a fixed bed guard reactor of reduced size, said reactors being disposed in series for use in a cyclic manner in accordance with a sequence of steps as described below.

Figure 1:
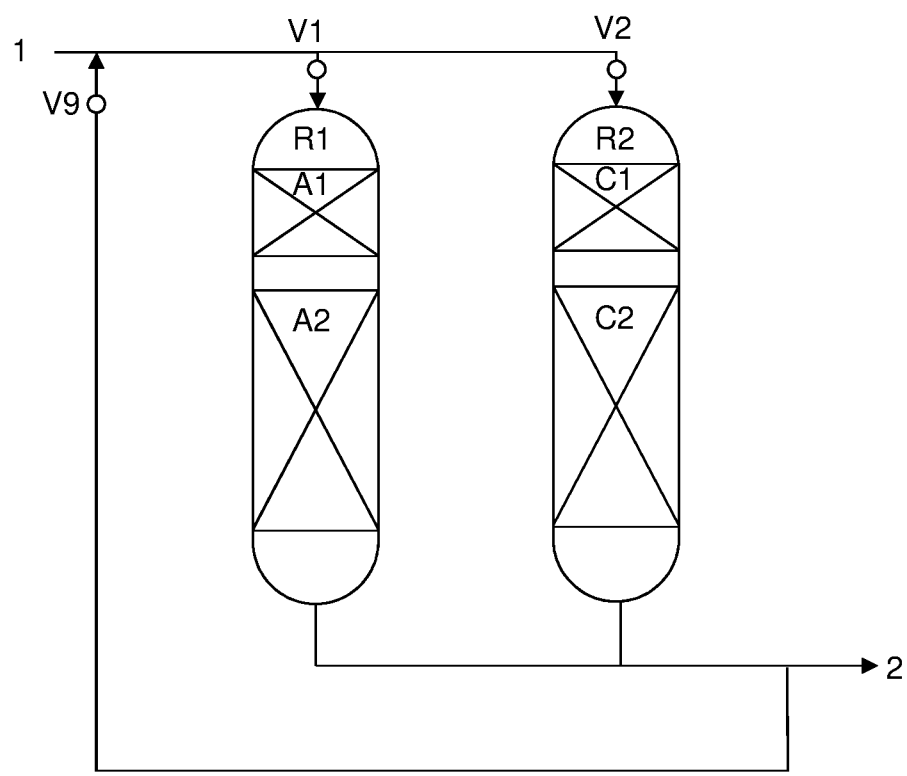
FIG. 1 represents a prior art process.

As can be seen in FIG. 1, conventional selective hydrogenation processes comprise two hydrogenation reactors: a first principal reactor R1 containing the catalytic beds A1 and A2, and in parallel, a second principal reactor R2 of identical size containing the catalytic beds C1 and C2.

In this process, a hydrocarbon feed is mixed with a gaseous phase comprising hydrogen and this mixture 1 is introduced into the head of the hydrogenation reactor R1 which is operated under hydrogenation conditions. The valve V1 is thus open, and the valve V2 is closed. The feed passes successively through the catalytic beds A1 and A2 and the selectively hydrogenated effluent 2 is recovered from the bottom of the reactor R1.

A portion of the liquid phase containing the hydrogenated olefinic feed may be recycled, after optionally having been cooled, via the valve V9 to the inlet to reactor R1, for mixing, along with the feed to be hydrogenated, with the gaseous phase comprising hydrogen.

When the reactor R1 starts to become deactivated, the feed is directed towards the second reactor R2. To this end, the valve V2 is open, and the valve V1 is closed. The feed is thus treated in the reactor R2 and passes successively through the catalytic beds C1 and C2 in order to recover the selectively hydrogenated effluent 2 from the bottom of reactor R2 while R1 is cleaned and its catalyst is regenerated. In the same manner, a portion of the liquid phase containing the hydrogenated olefinic feed may be recycled, after optionally having been cooled, via the valve V9 to the inlet to reactor R2 for mixing with the feed to be hydrogenated and the gaseous phase comprising the hydrogen.

Figure 2:
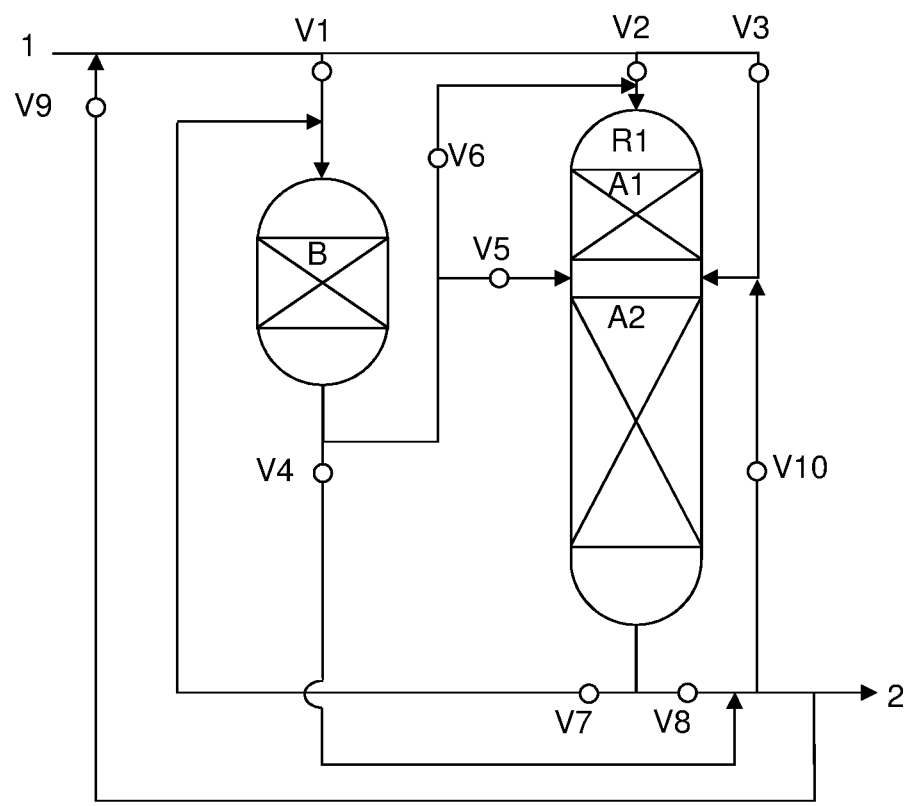
FIG. 2 represents a process of the invention.

In the context of the selective hydrogenation process in accordance with the invention, as illustrated in FIG. 2, a feed of hydrocarbons containing unsaturated molecules comprising at least 3 carbon atoms and a gaseous phase comprising hydrogen are passed, under hydrogenation conditions, over a hydrogenation catalyst in a single principal fixed bed reactor containing at least two catalytic beds and a fixed bed guard reactor which is smaller in size containing at least one catalytic bed, said reactors being disposed in series for use in a cyclic manner by repeating the steps a), b), c), c'), d) and d') defined below in succession:

- a step a), during which the feed passes in succession through all of the catalytic beds of the principal reactor, when the first catalytic bed of the principal reactor starts to become deactivated, a step b), during which the feed is introduced into the guard reactor then, by short-circuiting the first partially deactivated catalytic bed of the principal reactor, into the next non-deactivated catalytic bed of said principal reactor located immediately downstream with respect to the direction of movement of the feed,
- a step c), during which the feed passes uniquely and successively through all of the catalytic beds of the principal reactor,
- a step c'), simultaneously with step c), during which the deactivated catalyst of the catalytic bed or beds of the guard reactor is regenerated and/or replaced with fresh catalyst,
- a step d), during which the feed only passes through the guard reactor,
- a step d'), simultaneously with step d), during which the deactivated catalyst of the at least two catalytic beds of the principal reactor is regenerated and/or replaced with fresh catalyst.

During step a) of the process, the feed, already mixed with the gaseous phase comprising hydrogen, is introduced, via the line comprising a valve V2 which is open, into the reactor R1. During this period, the valves V1, V3, V4, V5, V6 and V7 are closed. The feed passes in succession through the catalytic beds A1 and A2 and the selectively hydrogenated effluent 2 is recovered from the bottom of the reactor R1 which is evacuated via the line comprising a valve V8 which is open.

A portion of the liquid phase containing the hydrogenated olefinic feed may be recycled, after optionally having been cooled, via the valve V9 to the inlet to reactor R1 for mixing, along with the feed to be hydrogenated, with the gaseous phase comprising hydrogen.

In accordance with another variation, a portion of the liquid phase containing the hydrogenated olefinic feed, after optionally having been cooled, may be recycled via the valve V10 to the inlet to catalytic bed A2.

Gradually over time, the catalytic beds, and in particular the first catalytic bed A1, will become deactivated during the step a). When the first catalytic bed A1 starts to become deactivated, step a) begins to be swung towards step b). This swing is carried out after an operating period for step a) which is between 10% and 70%, preferably between 20% and 60% of the maximum operating period $t_{Amax}$ for step a) for reaching the maximum tolerable value, as defined below.

During step b) of the process, the feed, already mixed with the gaseous phase comprising hydrogen, is introduced, via the line comprising a valve V1 which is open, into the guard reactor B. The effluent from the guard reactor, which is partially hydrogenated, is then introduced into the principal reactor upstream of the catalytic bed A2 via the line comprising a valve V5 which is open. During this period, the valves V2, V3, V4 and V6 are closed. The catalytic bed A1, partially deactivated during the step a), is thus short-circuited. The feed then passes through the catalytic bed A2 and the selectively hydrogenated effluent 2 is recovered from the bottom of the principal reactor R1 and is evacuated via the line comprising a valve V8 which is open.

A portion of the liquid phase containing the hydrogenated olefinic feed may be recycled, after optionally having been cooled, via the valve V7, or via the valve V9, to the inlet to the guard reactor B, for mixing, along with the feed to be hydrogenated, with the gaseous phase comprising hydrogen.

In accordance with another variation, a portion of the liquid phase containing the hydrogenated olefinic feed, after optionally having been cooled, may be recycled via the valve V10 to the inlet to catalytic bed A2.

Gradually over time, since the guard reactor B has been brought into contact with the feed, it will become deactivated during step b). When the catalyst of the catalytic bed or beds of the guard reactor has been completely deactivated, step b) starts to be swung towards step c). This swing is carried out after an operation time for step b) which is between 40% and 100%, preferably between 70% and 100% of the maximum operating period $t_{Bmax}$ for step b) for reaching the maximum tolerable value, as defined below.

During step c) of the process, the feed, already mixed with the gaseous phase comprising hydrogen, is introduced, via the line comprising a valve V2 which is open, into the reactor R1. During this period, the valves V1, V3, V4 V5, V6 and V7 are closed. The feed passes successively through the catalytic beds A1 and A2 and the selectively hydrogenated effluent 2 is recovered from the bottom of the reactor R1 which is evacuated via the line comprising a valve V8 which is open. Gradually over time, the catalytic beds, and in particular the first catalytic bed A1 which has been brought into contact with the feed, continue to become deactivated.

In accordance with a variation, a portion of the liquid phase containing the hydrogenated olefinic feed may be recycled, after optionally having been cooled, via the valve V9 to the inlet to reactor R1, for mixing, along with the feed to be hydrogenated, with the gaseous phase comprising hydrogen.

In accordance with another variation, a portion of the liquid phase containing the hydrogenated olefinic feed, after optionally having been cooled, may be recycled via the valve V10 to the inlet to catalytic bed A2.

Gradually over time, the catalytic beds of the principal reactor, and in particular the first catalytic bed A1, will become deactivated during step c). When the first catalytic bed A1 has been completely deactivated, step c) begins to be swung towards step d). This swing is carried out after an operating time for step c) which is between 90% and 100%, preferably 100% of the maximum operating period $t_{Cmax}$ for step c) for reaching the maximum tolerable value, as defined below.

During step c') of the process, which is carried out simultaneously with step c), the deactivated catalyst of the catalytic bed or beds of the guard reactor B is regenerated and/or replaced with fresh catalyst.

During step d) of the process, the feed, already mixed with the gaseous phase comprising hydrogen, is introduced, via the line comprising a valve V1 which is open, into the guard reactor B. The selectively hydrogenated effluent 2 is recovered from the bottom of the guard reactor B and is evacuated via the line comprising a valve V4 which is open. The feed thus only passes through the guard reactor. During this period, the valves V2, V3, V5, V6, V7, V8 and V10 are closed.

In accordance with a variation, a portion of the liquid phase containing the hydrogenated olefinic feed may be recycled, after optionally having been cooled, via the valve V9 to the inlet to the guard reactor, for mixing, along with the feed to be hydrogenated, with the gaseous phase comprising hydrogen.

In order to ensure a selective hydrogenation in the reduced volume of catalyst in the catalytic bed or beds of reactor B during this step, the operating conditions are preferably more severe than the operating conditions used at the start of step a) (or the operating conditions used at the start of the other steps b) and c) which are generally identical to those of step a). The need to modify or otherwise the operating conditions depends on the nature of the feed in particular. As an example, the heavier the feed or the more loaded it is with impurities, the more the operating conditions will need to be made more severe.

In accordance with a variation, and to make the operating conditions more severe and/or to improve the thermal control, it is possible to:
- increase the temperature of the guard reactor B during step d) and/or
- increase the flow of the phase comprising the hydrogen during step d) and/or
- reduce the flow rate of feed and/or
- increase the recycle flow rate.

In accordance with a variation, the temperature of the guard reactor B is increased. In this case, the increase in the temperature of the guard reactor B at the head of the reactor at the start of step d) with respect to the start of step a) is in the range 0.5° C. to 40° C., preferably in the range 3° C. to 20° C.

In accordance with another variation, it is also possible to reduce the flow rate of feed introduced into the guard reactor during the step d).

In accordance with yet another variation, it is possible to increase the recycle flow rate in order to improve the thermal control. The increase in the recycle flow rate at the start of step d) is in the range 0.5% to 100% with respect to the recycle flow rate to the principal reactor at the start of step a), preferably in the range 3% to 50%. The increase in the recycled flow rate may also be carried out with other means for making it more severe, such as increasing the temperature.

Preferably, the temperature is increased and/or the recycle flow rate is increased.

When the catalyst for the guard reactor B has been completely deactivated, step d) starts to be swung towards step a). This swing is carried out after an operating period for step d) which is between 70% and 100%, preferably between 85% and 100% of the maximum operating period $t_{Dmax}$ for step d) for reaching the maximum tolerable value, as defined below.

During step d') of the process, which is carried out simultaneously with step d), the deactivated catalyst of the at least two catalytic beds A1 and A2 of the principal reactor R1 is regenerated and/or replaced with fresh catalyst.

In accordance with a variation, a step a') may be carried out simultaneously with the step a), during which the catalyst of the catalytic bed or beds of the guard reactor deactivated during step d) is regenerated and/or replaced with fresh catalyst.

The cycle is then started again. The operations on the valves of the unit mean that the operation of the principal reactor R1 and of the guard reactor B are as shown in the table below:

| Step | Cycle | V1 | V2 | V4 | V5 | V8 |
|---|---|---|---|---|---|---|
| a | A1 + A2 | Closed | Open | Closed | Closed | Open |
| b | B + A2 | Open | Closed | Closed | Open | Open |
| c | A1 + A2 | Closed | Open | Closed | Closed | Open |
| d | B | Open | Closed | Open | Closed | Closed |
| a | A1 + A2 | Closed | Open | Closed | Closed | Open |

Size of the Guard Reactor

In order to benefit from the advantages of the process in accordance with the invention, it is important for the guard reactor B containing at least one catalytic bed to be smaller in size than the principal reactor.

More particularly, the total volume of catalyst contained in the catalytic bed or beds of the guard reactor is a maximum of 60%, preferably a maximum of 50%, and particularly preferably a maximum of 40% of the total volume of catalyst contained in the catalytic beds of the principal reactor.

The guard reactor B may contain one or more catalytic beds. When it contains a plurality of catalytic beds, it may or may not be provided with a quench box between two catalytic beds.

This quench box may be supplied with a quench liquid such as fresh or recycled feed, and/or with a gaseous quench such as the gaseous phase containing hydrogen. Its flow rate of diluent (usually the recycle) may be equivalent or indeed higher than the flow rate of the feed, which means that the exothermicity can be reduced.

Deactivation Time

In the context of the invention, the catalyst or catalysts contained in the catalytic bed or beds of the principal reactor or of the guard reactor, in particular the first catalytic bed in the direction of movement of the feed, gradually becomes deactivated. When the catalyst(s) become(s) deactivated or partially deactivated, a swing from one step to another step is commenced.

The operating period for each of steps a), b), c) and d) is defined with respect to a maximum operating period for each step, which is itself defined with respect to a tolerable maximum value for a temperature or for a selectivity. The maximum tolerable value will already have been defined by the person skilled in the art and in particular depends on the nature of the feed to be treated, but also on the operating conditions and on the catalysts selected. When the maximum tolerable value is reached, the step must be swung, i.e. short-circuiting of a catalytic bed or disconnection of a reactor and/or connection to another reactor.

More particularly, for a C3 feed for which little or no change in temperature is observed during a cycle, the maximum tolerable value is the selectivity required by the specifications (generally corresponding to reaching equal composition of propylene between the inlet and the outlet of the reactor) at the end of the cycle. In fact, when the catalyst becomes deactivated, a gradual drop in selectivity is observed (formation of more and more propane, and reduction in the purity of propylene at the reactor outlet).

When the feed is a C4 feed, the maximum tolerable value is a temperature which is at 160° C., preferably 120° C. at the reactor outlet at the end of the cycle. In fact, above this temperature, a reduction in the selectivity of the hydrogenation reaction (oligomer formation) is observed. This range of temperatures is also the maximum which can be tolerated for a C5 feed, again because of a drop in the selectivity.

When the feed is a pyrolysis gasoline feed, the maximum tolerable value is a temperature which is at approximately 200° C., preferably 180° C. at the outlet from the reactor at the end of the cycle. In fact, above this temperature, a reduction in selectivity (hydrogenation of aromatics) is observed—this is also accompanied by a high risk of runaway.

The maximum operating period $t_{max}$ for each of steps a), b) c) and d) is thus defined as the time at which the maximum tolerable value for the temperature or the selectivity is reached. As an example, in the case of a pyrolysis gasoline feed, the maximum operating period $t_{Amax}$ for step a) is the time required to reach the maximum tolerable value of 180° C. and the maximum operating period $t_{Bmax}$ for step b) is the time required to reach the maximum tolerable value of 180° C., and so on. The maximum operating period for each of the steps may be different since they are dependent on the configuration of the facility and on the deactivation of the catalyst at the start of the step.

The operating period for each of steps a), b), c) and d) is thus respectively:

for step a): between 10% and 70%, preferably between 20% and 60% of $t_{Amax}$
for step b): between 40% and 100%, preferably between 70% and 100% of $t_{Bmax}$
for step c): between 90% and 100%, preferably 100% of $t_{Cmax}$
for step d): between 70% and 100%, preferably between 85% and 100% of $t_{Dmax}$.

Thus, for example, step a), during which the feed passes through the catalytic beds A1 and A2 of the principal reactor is swung into step b), during which the feed passes through the guard reactor B then the catalytic bed A2 of the principal reactor, after an operating period for step a) which is in the range 10% to 70%, preferably in the range 20% to 60% of the maximum operating period $t_{Amax}$ for reaching the maximum tolerable value during this step a) (for example 180° C. for a feed of pyrolysis gasoline). In fact, the swing of step a) towards step b) is carried out when the first catalytic bed A1 has been partially deactivated, which is expressed by an operating period for step a) which is between 10% and 70% of $t_{Amax}$.

In a preferred embodiment, the catalytic beds contained in the principal reactor may have different or identical volumes, but the preferred condition is that the volume of the last bed should be larger than each volume of the other beds. Preferably, the catalytic beds in the principal reactor have increasing volumes in the direction of flow. In fact, because the temperature rise due to the exothermicity of the hydrogenation reactions generally occurs on the first catalytic bed, it is advantageous to minimize the volume of this first bed.

Hydrogenation Conditions

In the context of the process in accordance with the invention, the polyunsaturated feed is brought into contact with a gaseous phase comprising hydrogen in the presence of a hydrogenation catalyst under conditions, in particular temperature, pressure and hourly space velocity (HSV), which allow hydrogenation.

In particular, the selective hydrogenation process is advantageously carried out under pressure, in a mixed gas/liquid phase, in the presence of hydrogen.

The selective hydrogenation process in accordance with the invention is preferably carried out in each reactor at a temperature of 0° C. to 200° C.

The pressure in each reactor is preferably in the range 1 to 6.5 MPa, more preferably in the range 1.5 to 5 MPa, and still more preferably in the range 1.5 to 3.5 MPa.

The overall hourly space velocity (HSV), defined as the ratio of the volume flow rate of fresh feed at 15° C. to the total volume of catalyst present in all of the reactors employed, is generally from 1 $h^{-1}$ to 100 $h^{-1}$, preferably from 1 $h^{-1}$ to 50 $h^{-1}$.

When the feed is a C3 feed, the selective hydrogenation process is usually carried out as a process in the gaseous phase or in a mixed gaseous/liquid phase with an overall hourly space velocity of 5 $h^{-1}$ to 30 $h^{-1}$, at a temperature of 0° C. to 70° C., and at a pressure in the range 1.5 to 5 MPa. The recycle ratio, defined as the ratio of the mass flow rate of recycle to the mass flow rate of feed entering the reactor, may in particular be in the range 0 to 5.

When the feed is a C4 feed, the selective hydrogenation process is usually carried out as a mixed gaseous/liquid phase process with an overall hourly space velocity of 2 $h^{-1}$ to 15 $h^{-1}$, at a temperature of 30° C. to 160° C., and at a pressure in the range 1.5 to 5 MPa. The recycle ratio, defined as the ratio of the mass flow rate of recycle to the mass flow rate of feed entering the reactor, may in particular be in the range 0 to 30.

When the feed is a C5 feed, the selective hydrogenation process is usually carried out as a mixed gaseous/liquid phase process with an overall hourly space velocity of 1 $h^{-1}$ to 10 $h^{-1}$, at a temperature of 30° C. to 160° C., and at a pressure in the range 1.5 to 5 MPa. The recycle ratio, defined as the ratio of the mass flow rate of recycle to the mass flow rate of feed entering the reactor, may in particular be in the range 0 to 15, preferably in the range 0.5 to 15.

Highly preferably, a selective hydrogenation process is carried out in which the feed is a steam cracked gasoline comprising polyunsaturated compounds, the (hydrogen)/(polyunsaturated compounds to be hydrogenated) molar ratio is generally in the range 1 to 2, the temperature is generally in the range 40° C. to 200° C., preferably in the range 50° C. to 180° C., the hourly space velocity (HSV) is generally in the range 1 $h^{-1}$ to 6 $h^{-1}$ and the pressure is generally in the range 2 MPa to 6 MPa. The hydrogen flow rate is adjusted in order to provide a sufficient quantity to theoretically hydrogenate all of the polyunsaturated compounds and to maintain an excess of hydrogen at the reactor outlet. The recycle ratio, defined as the ratio of the mass recycle flow rate to the mass flow rate of feed entering the reactor, may in particular be in the range 0 to 5, preferably in the range 0.5 to 5.

The operating conditions in the principal reactor and the guard reactor may be identical or different during steps a), b), c) and d); preferably, they are identical, in particular during steps a) and b) and c).

Similarly, the operating conditions in the principal reactor may be identical or different during steps a) and c).

In order to ensure selective hydrogenation in the reduced volume of catalyst in the catalytic bed or beds of reactor B during step d) when the feed only passes through the guard reactor and the catalyst in the principal reactor is replaced and/or regenerated, the operating conditions in step d) are preferably more severe than the operating conditions used at the start of step a) (or b) and c)) involving a step for selective hydrogenation as defined above.

Feed

Said hydrocarbon feed comprises at least one polyunsaturated molecule comprising at least 3 carbon atoms. More precisely, said polyunsaturated hydrocarbons present in said treated feed are in particular compounds comprising at least one acetylene function (i.e. at least one triple bond) and/or at least one diene function (i.e. at least two double bonds) and/or at least one alkenyl-aromatic function (i.e. at least one aromatic ring containing at least one olefinic ligand). In particular, said feed of polyunsaturated hydrocarbons may comprise at least one type of compound containing both an acetylene function and a diene function per molecule.

More particularly, the feed of hydrocarbons is selected from the group constituted by a C3 cut from steam cracking, a C4 cut from steam cracking, a C5 cut from steam cracking and a steam cracked gasoline, also known as a pyrolysis gasoline. The pyrolysis gasoline feed may also comprise alkenylaromatics.

The C3 cut from steam cracking advantageously used to carry out the selective hydrogenation process in accordance with the invention generally comprises propylene, propadiene, methylacetylene and propane. The C3 cut has the following average composition, for example: of the order of 90% by weight of propylene, of the order of 2% to 8% by weight of propadiene and methylacetylene, the remainder essentially being propane. In certain C3 cuts, between 0.1% and 2% by weight of C2 compounds and of C4 compounds may also be present.

The C4 cut from steam cracking advantageously used to carry out the selective hydrogenation process in accordance with the invention generally comprises butane, butene, butadiene, vinylacetylene and butyne. The C4 cut has the following average composition, for example: 1% by weight of butane, 46.5% by weight of butene, 51% by weight of butadiene, 1.3% by weight of vinylacetylene (VAC) and 0.2% by weight of butyne. In certain C4 cuts, between 0.1% and 2% by weight of C3 compounds and of C5 compounds may also be present.

The C5 cut from steam cracking advantageously used to carry out the selective hydrogenation process in accordance with the invention generally comprises pentanes, pentenes and pentadienes. The C5 cut has the following composition, for example: 21% by weight of pentanes, 45% by weight of pentenes, 34% by weight of pentadienes.

The steam cracked gasoline or pyrolysis gasoline advantageously used to carry out the selective hydrogenation process in accordance with the invention corresponds to a hydrocarbon cut with a boiling point which is generally in the range 0° C. to 250° C., preferably in the range 10° C. to 220° C. The polyunsaturated hydrocarbons to be hydrogenated present in said steam cracked gasoline are in particular diolefin compounds (butadiene, isoprene, cyclopentadiene, etc), styrene compounds (styrene, alpha-methyl styrene, etc) and indene compounds (indene, etc). The steam cracked gasoline generally comprises the C5-C12 cut with traces of C3, C4, C13, C14, C15 (for example between 0.1% and 3% by weight for each of these cuts). As an example, a feed formed from pyrolysis gasoline generally has the following composition, as a % by weight: 5% to 15% by weight of paraffins, 50% to 65% by weight of aromatic compounds, 5% to 15% by weight of monoolefins. 15% to 25% by weight of diolefins, 2% to 8% by weight of alkenylaromatic compounds and 20 to 300 ppm by weight of sulphur (parts per million), or even up to 2000 ppm of sulphur for certain difficult feeds, the total for the compounds being 100%.

Preferably, the feed of polyunsaturated hydrocarbons treated in accordance with the selective hydrogenation process of the invention is a steam cracked gasoline.

When said feed is a C3 cut, the selective hydrogenation process in accordance with the invention is intended to selectively hydrogenate propadiene and methylacetylene. In the case of a C4 cut, the intention is to eliminate the butadiene, vinylacetylene (VAC) and butyne; in the case of a C5 cut, pentadienes are intended to be eliminated. When said feed is a steam cracked gasoline, the selective hydrogenation process in accordance with the invention is intended to selectively hydrogenate said polyunsaturated hydrocarbons present in said feed to be treated in a manner such that the diolefinic compounds are partially hydrogenated into monoolefins and that the styrene and indene compounds are partially hydrogenated into the corresponding aromatic compounds.

Gaseous Phase

In the context of the process in accordance with the invention, the hydrocarbon feed is brought into contact with a gaseous phase comprising hydrogen.

The gaseous phase is often composed of a mixture of hydrogen and at least one other gas, which is inert for the reaction depending on the purification process employed. This other gas may, for example, be selected from the group formed by methane, ethane, propane, butane, nitrogen, argon, carbon monoxide (a few ppm) and carbon dioxide. This other gas is preferably methane or propane, and more preferably is free from carbon monoxide.

The quantity of hydrogen is preferably slightly in excess with respect to the stoichiometric value, allowing for selective hydrogenation of the polyunsaturated compounds present in the hydrocarbon feed. In this embodiment, the excess hydrogen is generally in the range 1% to 50% by weight, preferably in the range 1% to 30% by weight.

The proportion of hydrogen in the gaseous phase is in particular 60% to 100% by weight, and usually in the range 80% to 99.99% by weight, the complement to 100% being one or more of the inert gases mentioned above.

In accordance with a particularly preferred embodiment of the invention, the gaseous phase is constituted by 100% by weight of hydrogen.

The gaseous phase comprising hydrogen is preferably introduced at least to the head of the first reactor through which the feed passes, and may advantageously also be introduced to the head of each catalytic bed.

By staging the introduction of the gaseous phase comprising hydrogen between the various reactors in this manner, it is possible to introduce smaller quantities of hydrogen to the head of each reactor, which limits the risk of secondary reactions in each reactor. Furthermore, the introduction of a gaseous phase comprising hydrogen to the head of each reactor and at a temperature close to ambient temperature (approximately 20° C.) means that the temperature of the feed introduced into the downstream reactor can be reduced (since the hydrogenation reaction is exothermic), thereby limiting vaporization of the olefinic feeds, which favours better selectivity. The conjunction of a small amount of hydrogen introduced and an olefinic feed which is kept liquid brings about better dissolution of hydrogen in the feed, so that the reactor approaches monophase liquid conditions. These conditions which are close to monophase conditions mean that the selectivity of the hydrogenation reactions can be further improved.

The gas phase comprising hydrogen may also be introduced in part as a mixture with the hydrocarbon feed before the first bed of catalyst, and in part before the subsequent bed or beds contained in said reactor (also known as a "quench"), in order to limit the temperature gradient of the exothermic hydrogenation reactions in the reactor.

Hydrogenation Catalyst

The groups for the chemical elements given below are in accordance with the CAS classification (CRC Handbook of Chemistry and Physics, published by CRC press, editor-inchief D. R. Lide, 81$^{st}$ edition, 2000-2001). As an example, group VIII in accordance with the CAS classification corresponds to metals from columns 8, 9 and 10 of the new IUPAC classification.

The catalyst used in the process in accordance with the invention is a catalyst which is known to the person skilled in the art for a selective hydrogenation process. It may preferably comprise at least one metal from group VIII, more preferably palladium or nickel.

The metal from group VIII, preferably palladium, may preferably be deposited as a shell at the periphery of the support (beads, extrudates). The shell distribution is well known to the person skilled in the art and can be used to improve the selectivity of the catalyst in the sense that the polyunsaturated molecules are indeed converted into monoolefins, but the monoolefins are not hydrogenated into alkanes.

When the metal from group VIII is palladium, the palladium content is in the range 0.01% to 2% by weight of the mass of catalyst, preferably 0.03% to 0.8% by weight.

When the metal from group VIII is nickel, the nickel content is in the range 1% to 50% by weight of the mass of the catalyst, preferably in the range 5% to 40% by weight, and more preferably in the range 7% to 30% by weight.

The values for "% by weight" are based on the elemental form of the metal from group VIII.

The catalyst in particular comprises a porous support formed by at least one simple oxide selected from alumina ($Al_2O_3$), silica ($SiO_2$), titanium oxide ($TiO_2$), cerine ($CeO_2$) and zirconia ($ZrO_2$). Preferably, said support is selected from aluminas, silicas and silica-aluminas. Particularly preferably, the porous support is an alumina.

The porous support may in particular be in the form of beads, extrudates, for example in the form of trilobes or quadrilobes, pellets or irregular non-spherical agglomerates the specific shape of which may result from a crushing step.

Highly advantageously, the support is in the form of beads or extrudates.

Preferably, the catalyst used may also comprise at least one dopant, belonging to column IB of the periodic table, which may preferably be selected from the group formed by gold, silver and copper, and more preferably silver. It may also comprise tin.

Preferably, the selective hydrogenation catalysts further comprise at least one metal selected from the group constituted by alkalis and alkaline-earths.

Prior to use in a selective hydrogenation process, the selective hydrogenation catalysts generally undergo at least one reduction treatment, optionally followed by a passivation, generally with sulphur.

Each catalytic bed contains at least one catalytic bed containing one or more catalysts, optionally supplemented with at least one inert layer at the head of the catalytic bed. The catalysts used in the catalytic bed or beds of the reactors may be identical or different. The catalyst used in the guard reactor may or may not be identical to the catalyst used in the principal reactor.

Regeneration/Reactivation

When the catalyst of one of the reactors becomes deactivated, it is regenerated and/or rejuvenated.

Regeneration of the catalyst may in particular be carried out at a temperature of 200° C. to 480° C., with a gradual staged increase of the temperature, under nitrogen, and with successive additions of steam (steam stripping) and oxygen (combustion). The catalyst is then reactivated under hydrogen, and optionally with the addition of sulphur-containing molecules, in order to regain its initial condition.

Rejuvenation of the catalyst (known as hot hydrogen stripping) may in particular be carried out at a temperature of 200° C. to 450° C., with a gradual staged increase of the temperature, under nitrogen and hydrogen.

A procedure of this type may in particular allow sintering of the metallic particles and degradation of the support to be limited.

Depending on the steps a) to d) under consideration, a choice between regeneration and rejuvenation may be made by the person skilled in the art. As an example, during step d'), the person skilled in the art will preferentially select regeneration of the catalyst.

The term "regenerated catalyst" as used in this text or "step in which the catalyst is regenerated" is intended to mean a regenerated and/or rejuvenated catalyst or a step in which the catalyst is regenerated and/or rejuvenated.

Recycling

In accordance with a preferred embodiment of the invention, a portion of the gas/liquid effluent obtained from the principal reactor or guard reactor may be returned (i.e. recycled) as a mixture with the feed to be hydrotreated.

In accordance with another preferred embodiment of the invention, a portion of the gas/liquid effluent obtained from the principal reactor or the guard reactor may be returned (i.e. recycled) to the inlet to said reactor and/or a reactor or catalytic bed which is located upstream, preferably a reactor or catalytic bed located immediately upstream.

The aim of these recycles is to dilute the feed at the inlet to the reactor, in order to limit the rise in temperature and thus the formation of oligomers (or gums).

The effluent obtained from the principal reactor or the guard reactor may undergo a separation of the gaseous phase (unreacted hydrogen) before being recycled, in order to recycle only the liquid phase.

When the process in accordance with the invention employs a recycle, the gaseous phase comprising hydrogen may be introduced before and/or after introducing the recycle.

In accordance with another embodiment, a quench may be introduced between two catalytic beds in the principal reactor or the guard reactor in order to reduce the temperature in the downstream catalytic bed. This quench may be a liquid quench such as fresh feed or recycle, and/or a gaseous quench such as the gaseous phase containing hydrogen.

In accordance with yet another embodiment, the process in accordance with the invention may be operated in downflow mode or upflow mode. When it is operated in upflow mode, the catalytic bed A1 of the principal reactor is thus located below the catalytic bed A2.

Heat Exchanger (Chiller)

In accordance with a preferred embodiment, the process in accordance with the invention may in particular employ one or more heat exchanger(s) (chiller) between each reactor in order to chill the effluent from the reactor located immediately upstream, and in particular between the guard reactor and the principal reactor. The temperature of the effluent is thus reduced in a manner such as to liquefy the olefins vaporized in the guard reactor B. This intermediate heat exchanger can thus be used to control the exothermicity.

When the process in accordance with the invention uses one or more heat exchanger(s), the gas phase comprising hydrogen may be introduced upstream and/or downstream of said exchanger.

In accordance with another embodiment, each of the recycles may be chilled by a heat exchanger before being introduced into a reactor.

OTHER EMBODIMENTS

Other embodiments of the process of the invention may also be envisaged for the treatment of more difficult feeds or to relieve a catalytic bed during the various steps, as illustrated in FIG. 2.

In accordance with one embodiment, the guard reactor may be used upstream of the principal reactor during step a) in order to treat more difficult feeds. The feed is thus introduced into the guard reactor B via the valve V1, then passes through the two catalytic beds A1 and A2 of the principal reactor via the valve V6. In this case, the valve V2 is closed during step a).

In accordance with another embodiment and in order to relieve the first catalytic bed A1 during step a) and/or to treat more difficult feeds, a portion of the feed may be introduced into the guard reactor via the valve V1 in addition to introducing it into the first catalytic bed via the valve V2 during step a). The feed is thus introduced in parallel into the guard reactor and into the first catalytic bed of the guard reactor, the valves V1, V2 and V5 are open, the valve V4 is closed.

In accordance with another embodiment and in order to use all of the catalytic capacity of the second catalytic bed A2 of the principal reactor during step a), a portion of the feed may be introduced into the second catalytic bed A2 via the valve V3 in addition to introducing it into the first catalytic bed A1 via the valve V2 during step a). The feed is thus introduced in parallel into the two catalytic beds A1 and A2 of the principal reactor. The valves V2 and V3 are open. In accordance with this embodiment, a portion of the effluent from the principal reactor may be recycled to the guard reactor B via the valve V7 in order to compensate for short-circuiting the catalytic bed A1 for a portion of the feed. In accordance with yet another embodiment, when the feed passes successively through the guard reactor B then the second catalytic bed of the principal reactor during step b), a portion of the feed may also be introduced onto the first partially deactivated catalytic bed A1 of the principal reactor. The feed is thus introduced in parallel into the guard reactor and into the first catalytic bed of the guard reactor, the valves V1, V2 and V5 are open, the valve V4 is closed.

In accordance with another embodiment, the selectivity of the hydrogenation may be reduced, with the aim of saturating the olefins until between 10% and 15% remains.

EXAMPLES

Example 1, in Accordance with the Prior Art

A feed of pyrolysis gasoline "PyGas" with a MAV of 210 (MAV stands for Maleic Anhydride Value and measures the diolefins content) and a bromine number of 81 (measures the olefins content), containing 3% of styrene (and 8% of C9+ styrene compounds) was treated using a hydrogenation process as illustrated in FIG. 1 under the following operating conditions:

Flow rate of feed: 17 t/h
Composition of the gaseous phase comprising hydrogen: 95% $H_2$, 5% $CH_4$
Total hydrogen flow rate: 0.4 t/h ($H_2$+$CH_4$)
HSV, defined as the ratio of the volume flow rate of fresh feed at 15° C. to the volume of catalyst: 1.5 $h^{-1}$
Volume of catalyst, 17 $m^3$ in a reactor with a 1000 mm diameter (1st principal reactor, active catalyst)
Quantity of catalyst, 17 $m^3$ in a reactor with a 1000 mm diameter ($2^{nd}$ principal reactor, inactive catalyst)
Recycle flow rate: 30 t/h
Absolute pressure at reactor inlet: 3 MPa (30 bars)
Temperature at reactor inlet: 60° C.

The aim of this example was to reduce the styrene content (and consequently the majority of diolefins which are easier to hydrogenate) to 0.5% by weight at the reactor outlet.

In this embodiment, a single reactor was used for hydrogenation. 100% of the desired conversion of styrene thus had to be carried out in this reactor.

The process in accordance with the present example could thus be used to hydrogenate the pyrolysis gasoline feed for a cycle time estimated to be 6 months which, with the $2^{nd}$ principal reactor, meant that all of the catalytic volume could be used over a period of 12 months.

| Step | Cycle | Period |
|------|-------|--------|
| a | 1st Principal reactor | 6 months |
| b | $2^{nd}$ Principal reactor | 6 months |
| a | 1st Principal reactor | 6 months |

Example 2 in Accordance with the Invention

The same olefinic feed as that treated in Example 1 (comparative) was treated using a hydrogenation process in accordance with the invention, comprising two reactors in series and in parallel, with or without a quench box, as illustrated in FIG. 2. A mass of catalyst which was reduced by 15% by volume (28 $m^3$ instead of 34 $m^3$) compared with that used in the two reactors of Example 1 was distributed to an extent of 70% in the principal reactor (30% in the first bed, 40% in the second) and 30% in the guard reactor. The process of Example 1 (comparative) and that of Example 2 (in accordance with the invention) were compared at iso-flow rate (30 t/h) and quality of feed and gas (0.4 t/h $H_2$—95%, $CH_4$—5%). The operating conditions were as follows:

the HSV of the principal reactor, defined as the ratio of the volume flow rate of fresh feed at 15° C. to the volume de catalyst of the principal reactor: 1.5 $h^{-1}$
Volume of catalyst, 20 $m^3$ in a 1000 mm diameter reactor (principal reactor, active catalyst)
Volume of catalyst, 8 $m^3$ in a 1000 mm diameter reactor (guard reactor, active catalyst)
Reactor diameters: 1000 mm
Recycle flow rate: 30 t/h
Absolute pressure in the reactors: 3 MPa (30 bars)
Inlet temperature in $1^{st}$ reactor: 60° C.

The aim in this example was to maintain the styrene conversion at 0.5% by weight at the process outlet for a longer period than the reference process, by means of a reorganization of the catalytic beds and an optimized sequencing of them, while reducing the total volume of catalyst (calculated as the sum of the volumes of the principal reactor and the guard reactor). The following table records the steps of the cycle using all of the catalyst.

| Step | Cycle | Period | V1 | V2 | V4 | V5 | V8 | Regeneration |
|---|---|---|---|---|---|---|---|---|
| a | A1 + A2 | 3.5 months | Closed | Open | Closed | Closed | Open | B |
| b | B + A2 | 3.5 months | Open | Closed | Closed | Open | Open | |
| c | A1 + A2 | 3.5 months | Closed | Open | Closed | Closed | Open | B |
| d | B | 3 months | Open | Closed | Open | Closed | Closed | A1 + A2 |
| a | A1 + A2 | 3.5 months | Closed | Open | Closed | Closed | Open | B |

The table below records, for each step, the maximum operating periods $t_{max}$, the operating periods (as a percentage) as well as the actual periods:

| Step | Cycle | $t_{max}$ | Operating period | Period |
|---|---|---|---|---|
| a | A1 + A2 | 7 months | 50% | 3.5 months |
| b | B + A2 | 7 months | 50% | 3.5 months |
| c | A1 + A2 | 3.5 months | 100% | 3.5 months |
| d | B | 3 months | 100% | 3 months |
| a | A1 + A2 | 7 months | 50% | 3.5 months |

During steps a) and c), the catalyst of the guard reactor B was regenerated, and during step d), the catalyst of the principal reactor R1 (A1+A2) was regenerated. The duration of step a) in this example was determined with respect to the maximum operating period $t_{Amax}$, which was 7 months with respect to a temperature of 180° C. at the end of the cycle. In fact, since the volumes of beds A1 and A2 were more than 20% of those of the comparative example, it was estimated that the deactivation was at a lower rate, which meant that a period of 3.5 months could be obtained for step a).

The duration of step b) was similar to that of step a) because the volume of catalyst in the guard reactor B in this case was equal to that of A1 and, taking into account the slight deactivation of bed A2, again a duration for the step which was evaluated to be 3.5 months was obtained.

The impact of the deactivation of A2 during step b) on the duration of step c) was slight, and the duration of the combined steps a) and c) was evaluated to be the duration of the conventional cycle of the reference example (Example 1), which corresponds for this volume of catalyst to 7 months, and thus to a duration for step c) of 3.5 months.

During step c), the catalyst for reactor B was regenerated or replaced and step d) was started off on a catalyst with maximum activity. Under these conditions, a starting temperature of 63° C. obtained the expected conversion (0.5% by weight of styrene at the outlet) for a smaller volume of catalyst. In order to improve the control of the exothermicity, it was possible to modify the quantity of diluent or to provide B with a quench box. The conversion was obtained for an effluent temperature limiting the duration of step d) to between 3 and 3.5 months.

The process in accordance with the invention (Example 2) can thus be used to increase the duration of the total service cycle of the catalyst by 12% to 15% (13.5 months instead of 12) while reducing the volume of catalyst by 15% by volume, as well as the size of the associated equipment.

The invention claimed is:

1. A process for the selective hydrogenation of a feed of hydrocarbons containing polyunsaturated molecules comprising at least 3 carbon atoms, in which said feed and a gaseous phase comprising hydrogen are passed, under hydrogenation conditions, over a hydrogenation catalyst in a single principal fixed bed reactor containing at least two catalytic beds and a fixed bed guard reactor which is smaller in size containing at least one catalytic bed, said reactors being disposed in series for use in a cyclic manner by repeating the steps a), b), c), c'), d) and d') defined below in succession:
   a step a), during which the feed passes in succession through all of the catalytic beds of the principal reactor, when the first catalytic bed of the principal reactor starts to become deactivated, a step b), during which the feed is introduced into the guard reactor then, by short-circuiting the first partially deactivated catalytic bed of the principal reactor, into the next non-deactivated catalytic bed of said principal reactor located immediately downstream with respect to the direction of movement of the feed,
   a step c), during which the feed passes uniquely and successively through all of the catalytic beds of the principal reactor,
   a step c'), simultaneously with step c), during which the deactivated catalyst of the catalytic bed or beds of the guard reactor is regenerated and/or replaced with fresh catalyst,
   a step d), during which the feed only passes through the guard reactor,
   a step d'), simultaneously with step d), during which the deactivated catalyst of the at least two catalytic beds of the principal reactor is regenerated and/or replaced with fresh catalyst.

2. The process as claimed in claim 1, in which the total volume of catalyst contained in the catalytic bed or beds of the guard reactor is a maximum of 60% of the total volume of catalyst contained in the catalytic beds of the principal reactor.

3. The process as claimed in claim 1, in which the hydrocarbon feed is selected from the group constituted by a C3 cut from steam cracking, a C4 cut from steam cracking, a C5 cut from steam cracking and a pyrolysis gasoline, and a mixture thereof.

4. The process as claimed in claim 1, in which a step a') is carried out simultaneously with step a), during which the catalyst deactivated during step d) of the catalytic bed or beds of the guard reactor is regenerated or replaced with fresh catalyst.

5. The process as claimed in claim 1, in which the period of operation for each of steps a), b), c) and d), defined with respect to a maximum operating period $t_{max}$ for each step, which is the time to reach a maximum tolerable value for a temperature or a selectivity for a given feed, is respectively:
   for step a): between 10% and 70% of $t_{Amax}$
   for step b): between 40% and 100% of $t_{Bmax}$
   for step c): between 90% and 100% of $t_{Cmax}$
   for step d): between 70% and 100% of $t_{Dmax}$.

6. The process as claimed in claim 5, in which:
   the maximum tolerable value for a C3 feed is the selectivity in accordance with the specifications in force;
   the maximum tolerable value for a C4 feed is a maximum temperature of 160° C.;
   the maximum tolerable value for a C5 feed is a maximum temperature of 160° C.;

the maximum tolerable value for a feed of pyrolysis gasoline is a maximum temperature of 200° C.

7. The process as claimed in claim 1, in which each reactor is operated at a temperature of 0° C. to 200° C., at a pressure in the range 1 to 6.5 MPa and at an overall hourly space velocity, defined as the ratio of the volume flow rate of the fresh feed at 15° C. to the total volume of catalyst present in the series of reactors employed, in the range 1 $h^{-1}$ to 100 $h^{-1}$.

8. The process as claimed in claim 1, in which a portion of the effluent obtained from the principal reactor or from the guard reactor is recycled as a mixture with the feed to be hydrogenated.

9. The process as claimed in claim 1, in which the operating conditions for hydrogenation during steps a) b) c) and d) are identical.

10. The process as claimed in claim 1, in which during step d), the temperature of the guard reactor is increased and/or the flow of the phase comprising hydrogen is increased, and/or the recycle flow rate into the guard reactor is increased and/or the flow rate of feed introduced into the guard reactor is reduced with respect to respectively the temperature, the flow or the flow rate(s) employed at the start of step a).

11. The process as claimed in claim 10, in which the increase in the temperature of the guard reactor at the head of the reactor at the start of step d) with respect to the start of step a) is in the range 0.5° C. to 40° C.

12. The process as claimed in claim 10, in which the increase in the recycle flow rate at the guard reactor at the start of step d) with respect to the recycle flow rate at the start of step a) is in the range 0.5% to 100%.

13. The process as claimed in claim 1, in which a quench is introduced between two catalytic beds in the principal reactor or the guard reactor, said quench possibly being a liquid quench and/or a gaseous quench.

14. The process as claimed in claim 1, in which one or more heat exchanger(s) is employed between the guard reactor and the principal reactor.

15. The process as claimed in claim 1, in which the hydrogenation catalysts used are identical or different in the catalytic bed or beds of the principal reactor and/or of the guard reactor.

* * * * *